United States Patent [19]

Ravichandran et al.

[11] Patent Number: 4,757,102

[45] Date of Patent: Jul. 12, 1988

[54] COMPOSITIONS STABILIZED WITH AMINOXY ALKYLAMINE DERIVATIVES

[75] Inventors: Ramanathan Ravichandran; Stephen D. Pastor, both of Yonkers; Thomas E. Snead, Dobbs Ferry, all of N.Y.

[73] Assignee: Ciba-Geigy Corporation, Ardsley, N.Y.

[21] Appl. No.: 861,960

[22] Filed: May 12, 1986

[51] Int. Cl.$^4$ ................................................. C08K 5/34
[52] U.S. Cl. ........................................ 524/95; 524/96; 524/97; 524/98; 524/99; 524/100; 524/101; 524/102; 524/103; 524/104; 524/105; 524/131; 524/136; 524/219; 524/236; 524/239; 524/289; 524/291; 524/342; 524/343; 524/349; 544/398; 252/401; 252/403
[58] Field of Search .................. 524/95–100, 524/236, 131, 136, 219, 236, 239, 289, 291, 342, 343, 349; 544/398; 252/401, 403

[56] References Cited

U.S. PATENT DOCUMENTS

| | | | |
|---|---|---|---|
| 2,990,406 | 6/1961 | Jones | 524/100 |
| 3,384,613 | 5/1968 | Parks | 524/236 |
| 3,756,969 | 9/1973 | Danielson | 524/100 |
| 4,068,070 | 1/1978 | Sakai et al. | 544/398 |
| 4,240,954 | 12/1980 | Stretanski | 524/100 |

OTHER PUBLICATIONS

Bernhart, et al., Tetrahedron Letters, No. 29, pp. 2493–2496 (1974).
Zinner, et al., Chem. Berichte 99, pp. 895–902 (1966).

*Primary Examiner*—John Kight
*Assistant Examiner*—Kriellion Morgan
*Attorney, Agent, or Firm*—Harry Falber

[57] ABSTRACT

Various substituted aminoxy alkylamine derivatives are effective in stabilizing organic materials against oxidative, thermal and actinic degradation, said derivatives being particularly effective as color improvers and process stabilizers in organic materials containing phenolic antioxidants and/or metal salts of fatty acids and/or hindered amine light stabilizers and/or organic phosphorus compounds; and certain of said derivatives as new compounds.

21 Claims, No Drawings

COMPOSITIONS STABILIZED WITH AMINOXY ALKYLAMINE DERIVATIVES

Organic polymeric materials such as plastics and resins are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various organic hydroxylamine compounds are generally known and some are commercially available. A number of patents disclose nitrogen-substituted hydroxylamines as antioxidant stabilizers for various substrates including polyolefins, polyesters and polyurethanes. U.S. Pat. Nos. 3,432,578, 3,644,278, 3,778,464, 3,408,422, 3,926,909, 4,316,996 and 4,386,224 are representative of such patents which basically disclose N,N-dialkyl-, N,N-diaryl- and N,N-diaralkyl hydroxylamine compounds and their color improvement and color stabilizing activity.

In addition, Zinner et al, Chem. Berichte 99, 895 (1966) describe the Mannich-type condensation reactions of selected N-hydroxy-dialkylamines, formaldehyde and secondary amines. Most of the resulting compounds are low molecular weight. Typical formulae include $R_2NOCH(R)NR_2''$ and $(R_2NOCH_2)_2N-CH_3$ with the various R groups being lower alkyl, benzyl, cyclohexyl and heterocyclic. No practical utility is disclosed for these compounds. Bernhart et al, Tetrahedron Letters 29, 2493-2496 (1974) discloses the compound $C_6H_5CH_2-NH-OCH_2CH_2N(C_2H_5)_2$ for a pharmacological utility.

It has now been determined that the compositions of this invention exhibit a variety of desirable properties stemming from the presence therein of the indicated aminoxy alkylamine derivatives. Thus, the compounds serve to protect various substrates such as polyolefins, elastomers and lubricating oils against the adverse effects of oxidative and thermal degradation. They are most effective as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine light stabilizers or combinations of phenolic antioxidants and organic phosphites. In addition, the gas fading that may be experienced upon exposure to the combustion products of natural gas is also significantly reduced.

It is a primary object of this invention to provide compositions of organic materials stabilized against oxidative, thermal and actinic degradation by the presence therein of a class of substituted aminoxy alkylamine derivatives.

It is a further object to provide such compositions which also contain phenolic antioxidants wherein said derivatives substantially reduce color formation resulting from the presence of said phenols.

It is still a further object to provide a novel class of aminoxy alkylamine derivatives which likewise exhibits a broad range of improved stabilization performance characteristics.

Various other objects and advantages of this invention will become evident from the following description thereof.

The stabilizing compounds utilized in the compositions of this invention correspond to the formula

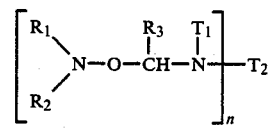

wherein $R_1$ and $R_2$ are independently alkyl of 1 to 36 carbon atoms, cycloalkyl of 5 to 12 carbon atoms, aralkyl of 7 to 9 carbon atoms or said aralkyl substituted by alkyl of 1 to 36 carbon atoms, or $R_1$ and $R_2$ together with the nitrogen can form a 5-7 member heterocyclic ring, or $R_1$ and $R_2$ are independently a group of the formula

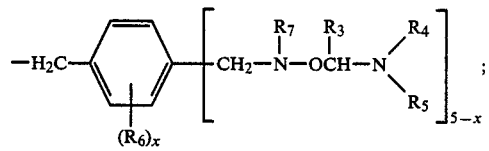

$R_3$, $R_4$, $R_5$, $R_6$ and $R_7$ are independently hydrogen, alkyl of 1 to 36 carbon atoms, cycloalkyl of 5 to 12 carbon atoms, allyl, aryl, aralkyl of 7 to 9 carbon atoms, said aralkyl substituted by alkyl of 1 to 36 carbon atoms, bornyl, norbornyl or isobornyl, or $R_4$ and $R_5$ together with nitrogen can form a 5-7 member heterocyclic ring;

n is 1-4;

x is 0-5;

$T_1$ is $R_3$ or

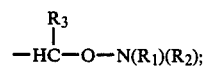

when n=1, $T_2$ is $R_3$ or 5-7 member unsaturated heterocyclic-substituted ($C_1$-$C_4$)alkyl, or $T_1$ and $T_2$ together with the nitrogen can form a 5-7 member saturated heterocyclic ring;

when n=2, $T_2$ is alkylene of 2 to 12 carbon atoms, cycloalkylene of 6 to 10 carbon atoms, arylene of 6 to 10 carbon atoms or alkylenearylenealkylene of 8 to 10 carbon atoms or $T_1$ and $T_2$ together with the two nitrogens can form a 5-7 member saturated heterocyclic ring;

when n=3, $T_2$ is alkanetriyl of 3 to 6 carbon atoms or $T_1$ and $T_2$ together with the three nitrogens can form a 5-6 member saturated heterocyclic ring; and when n=4, $T_2$ is alkanetetriyl of 4 to 6 carbon atoms.

Representative $R_1$–$R_7$ groups are straight-chain or branched alkyl with 1 to 18 carton atoms such as methyl, ethyl, n-propyl, n-butyl, tert.butyl, n-pentyl, n-octyl, 2-ethylhexyl, decyl, dodecyl and octadecyl; cyclopentyl or cyclohexyl; and benzyl, α-methylbenzyl and α,α-dimethylbenzyl. $R_1$ and $R_2$ as benzyl or substituted benzyl and $R_3$ as hydrogen are preferred. $R_1/R_2$ and $R_4/R_5$ heterocyclic groups include piperidyl, pyrryl, morpholino or pyrrolidino. $T_1$ is preferably one of the above noted $R_1$–$R_7$ representative groups or the substituted aminoxy group, while $T_2$ when $n=1$, is also preferably one of the above noted $R_1$–$R_7$ representative groups or pyridin-2-yl alkyl. $T_1/T_2$ ($n=1$) includes pyrrolidino, piperidyl and morpholino. $T_2$ when $n=2$ is, for example, ethylene, propylene, hexamethylene, phenylene and xylylene, and $T_1/T_2$ heterocyclic is for example, piperazine or pyrazolidine. $T_2$ when $n=3$ is, for example, trimethylylpropane and $T_1/T_2$ heterocyclic is fully saturated triazine or triazole. $T_2$ when $n=4$ is, for example, pentaerythrityl.

Typical $n=2$ and 3 heterocyclic compounds are

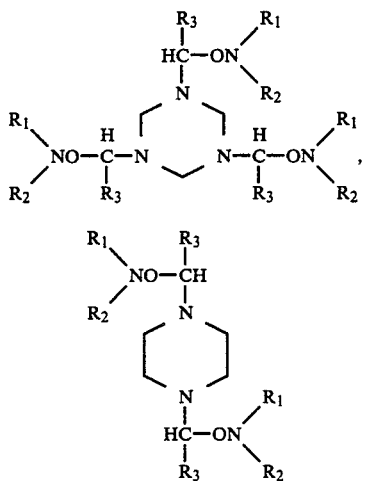

These compounds can be prepared by reacting the appropriately substituted hydroxylamine with the appropriate nitrogen-containing compound in the presence of an aldehyde such as formaldehyde, and a solvent such as acetonitrile, methylene chloride or an alcohol such as methanol. The nitrogen-containing compound can be an amine such as di-n-butylamine, di-n-hexylamine, di-n-octylamine, diphenylamine, diallylamine or 1,6-hexanediamine, or a heterocyclic compound such as piperidine, piperazine, aminoalkyl pyridine, hexahydro-s-triazine or amino-substituted norbornane. The reaction temperature ranges from 0° to 80° C. The starting materials needed to prepare the stabilizers are items of commerce or can be prepared by known methods.

When preparing compounds where $R_1$ and/or $R_2$ are the aminoxy-substituted benzyl moiety, x is preferably 1 or 2 and the compounds are prepared by the reaction of the appropriately substituted hydroxylamine, formaldehyde and a secondary mono- or diamine in the presence of a solvent, e.g. acetonitrile or methanol.

The compounds utilized in the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include

1. Polymers of monoolefins and olefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkl acrylate or acrylonitrile/vinyl halogenide copolymers or acrylonitrile/alkyl methacrylate/butadiene terpolymer.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as iolyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyl resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thiobis-(6-tert.butyl-4-methylphenol)
2,2'-thiobis-(4-octylphenol)
4,4'-thiobis-(6-tert.butyl-3-methylphenol)
4,4'-thiobis-(6-tert.butyl-2-methylphenol)
4,4'-thiobis-(4,6-di-tert.butylphenol)
4,4'-thiobis-(4,6-dimethylphenol)

1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4 methyl-6-cyclohexylphenol)
2,2'-methylene-bis-(6-nonyl-4-methylphenol)
2,2'-methylene-bis-[6-(α-methylbenzyl)-4-nonylphenol]

2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethyleneglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxyl-2,6-dimethylbenzyl-)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |
| N—methyldiethanol | |

1.8. Esters of β-(5-tert.butyl-4-hydroxy-3-methylphenyl)propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |
| N—methyldiethanol | |

1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-5-chloro-3'-tert.butyl-5'-methyl-, 3'-sec.butyl-5'-tert.butyl-, 4'-octoxy, 3',5'-di-tert.amyl-,3',5'-bis-(α,α-dimethylbenzyl)-derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butylphenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triathanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, coniensation product of N,N'-(2,2,6,6-tetramethylpiperidyl)-hexamethylendiamine and 4-tert.octylamino-2,6-dichloro-1,3,5-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbitol triphosphite, tetrakis-(2,4-di-tert.butylphenyl)-4,4′-diphenylylenediphosphonite, substituted dibenzo[d,g][1,3,2]dioxophosphorins, substituted dibenzo[d,f][1,3,2]dioxaphosphepins, substituted dibenzo[c,e][1,3,2]oxaphosphorins.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

While the instant aminoxy alkylamines can be beneficially used as stabilizers for a variety of substrates, particularly the polyolefins, both alone and in conjunction with other coadditives, the introduction of the instant aminoxy alkylamines into polyolefins, optionally containing various alkali metal, alkaline earth metal and aluminum salts of higher fatty acids (see Additive #7 hereinabove), with hindered phenolic antioxidants exhibits enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert- butyl-4-hydroxybenzylphosphonate, 1,3,5-tris(3,5-di-tert-butyl-4-hydroxybenzyl-)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2′-ethylidene-bis(4,6-di-tert-butylphenol), 1,3,5-tris-(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N′-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N′-bis-[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5trimethyl-2,4,6-tris(3,5-di-tert-butyl-4hydroxybenzyl)benzene, 1 -di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert.butyl-p-cresol or 2,2′-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di.tert-butyl-4-hydroxybenzyl) malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylarino-s-triazine with N′-(2,2,6,6-tetramethyl-4-piperidyl)hexamethylene diamine.

As previously noted, certain aminoxy alkylamine derivatives also form part of the instant invention. These derivatives correspond to the formula

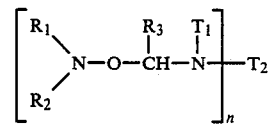

wherein
n is 1–4;
when n=1, $R_1$ and $R_2$ are independently a group of the formula

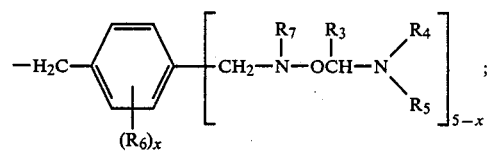

$R_3$, $R_4$, $R_5$, $R_6$ and $R_7$ are independently hydrogen, alkyl of 1 to 36 carbon atoms, cycloalkyl of 5 to 12 carbon atoms, allyl, aryl, aralkyl of 7 to 9 carbon atoms, said aralkyl substituted by alkyl of 1 to 36 carbon atoms, bornyl, norbornyl or isobornyl, or $R_4$ and $R_5$ together with nitrogen can form a 5-7 member heterocyclic ring; x is 1–5;
$T_1$ is $R_3$ or

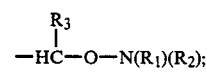

$T_2$ is $R_3$ or 5-7 member unsaturated heterocyclic-substituted $(C_1–C_4)$alkyl, or $T_1$ and $T_2$ together with the nitroger can form a 5-7 member saturated heterocyclic ring; and when n is 2–4, R₁ and R₂ are independently alkyl of 1 to 36 carbon atoms, cycloalkyl of 5 to 12 carton atoms, aralkyl of 7 to 9 carbon atoms or said aralkyl substituted by alkyl of 1 to 36, or R₁ and R₂ together with the nitrogen can form a 5-7 member heterocyclic ring, or R₁ and R₂ are independently a group of the formula

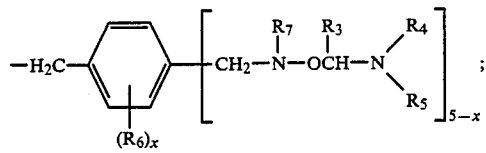

R₃, R₄, R₅, R₆ and R₇ are independently hydrogen, alkyl of 1 to 36 carbon atoms, cycloalkyl of 5 to 12 carbon atoms, allyl, aryl, aralkyl of 7 to 9 carbon atoms, said aralkyl substituted by alkyl of 1 to 36 carbon atoms, bornyl, or norbornyl or isobornyl, or R₄ and R₅ together with nitrogen can form a 5-7 member heterocyclic ring; x is 0–5; and T₁ is R₃ or

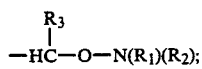

when n=2, T₂ is alkylene of 2 to 12 carbon atoms, cycloalkylene of 6 to 10 carbon atoms, arylene of 6 to 10 carbon atoms or alkylenearyleneal kylene of 8 to 10 carbon atoms or T₁ and T₂ together with the two nitrogens can form a 5-7 member saturated heterocyclic ring;

when n=3, T₂ is alkanetriyl of 3 to 6 carbon atoms or T₁ and T₂ together with the three nitrogens can form a 5-7 member saturated heterocyclic ring; and when n=4, T₂ is alkanetetrayl of 4 to 6 carbon atoms.

The following examples illustrate the embodiments of this invention. Thus, they describe the preparation of various aminoxy alkylamine derivatives, including those forming part of the invention, and of stabilized compositions. In these examples, all parts given are by weight unless otherwise specified.

EXAMPLE I

[N-N-Dibenzylaminoxymethyl]piperidine

A solution of 21.33 g of dibenzylhydroxylamine in 50 ml of acetonitrile containing 8.0 g of aqueous formaldehyde (37%) solution is admixed with 8.7 g of piperidine and the solution is stirred at room temperature for 24 hrs. The precipitated product is removed by filtration and recrystallized from acetonitrile, mp 57°–60° C.

Anal. Calcd. for $C_{20}H_{26}N_2O$: C, 77.4; H, 8.4; N, 9.0
Found: C, 77.1; H, 8.4; N, 9.0

EXAMPLE II 1,4-Bis[N,N-Dibenzylaminoxymethyl]piperazine

The procedure of Example I is repeated using 21.33 g of dibenzylhydroxylamine, 8.2 ml of aqueous formaldehyde (37%) solution and 4.31 g of piperazine. Recrystallization of the crude product from acetonitrile affords 21.8 g of the title compound as a white solid, mp 132°–35° C.

Anal. Calcd. for $C_{34}H_{40}N_4O_2$; C, 76.1; H, 7.5; N, 10.4
Found: C, 76.0; H, 7.7; N, 10.5

EXAMPLE III

[N,N-Dibenzylaminoxymethyl]dimethylamine

A mixture of 4.86 g of dibenzylhydroxylamine, 2.42 g of anhydrous sodium carbonate and 4.22 g of N,N-dimethylmethyleneammoniumiodide in 50 ml of methylene chloride is stirred at room temperature under N₂ for 48 hrs. After removal of the insoluble inorganic residue by filtration, the solution is concentrated under reduced pressure. The resulting residue is treated with heptane to extract the product. Removal of the combined heptane extracts affords the product as a thick oil.

Anal. Calcd. for $C_{17}H_{22}N_2O$: C, 75.5; H, 8.2; N, 10.4
Found: C, 75.4; H, 8.2; N, 9.8

EXAMPLE IV

[N,N'-Dimethyl-N,N'-bis(dibenzylaminoxymethyl)]-hexa methylenediamine

The procedure of Example I s repeated using 21.33 g of dibenzylhydroxylamine, 8.2 ml of aqueous formaldehyde (37%) solution and 7.36 g of N,N'-dimethyl-1,6-hexanediamine in 100 ml of acetonitrile. to yield 26.6 g of product as a colorless liquid.

Anal. Calcd. for $C_{38}H_{50}N_4O_2$: C, ;6.7; H, 8.5; N, 9.4
Found: C, 76.1; H, 8.5; N, 9.4

EXAMPLE V

[N,N-Dibenzylaminoxymethyl]di-n-octylamine

The procedure of Example I is repeated using 21.33 g of dibenzylhydroxylamine, 9.73 g of aqueous formaldehyde (37%) solution and 24.15 g of di-n-octylamine in acetonitrile to afford the title compound.

Anal. Calcd. for $C_{31}H_{50}N_2O$: C, 79.8; H, 10.8; N, 6.0
Found: C, 79.6; H, 10.6; H, 5.9

EXAMPLE VI

[N,N-Dibenzylaminoxymethyl]di-n-butylamine

The procedure of Example I is repeated using 21.33 g of dibenzylhydroxylamine, 9.73 g of aqueous formaldehyde (37%) solution and 12.93 g of di-n-butylamine in acetonitrile to afford the title compound.

Anal. Calcd. for $C_{23}H_{34}N_2O$: C, 77.9; H, 9.7; N, 7.9
Found: C, 78.2; H, 9.4; H, 7.9

EXAMPLE VII

[N,N-Dibenzylaminoxymethyl]di-n-hexylamine

The procedure of Example I is repeated using 21.33 g of dibenzylhydroxylamine, 9.73 g of aqueous formaldehyde (37%) solution and 18.54 g of di-n-hexylamine, to afford the title compound.

Anal. Calcd. for $C_{27}H_{42}N_2O$: C, 79.0; H, 10.3; N, 6.8
Found: C, 79.2; H, 10.3; H, 6.8

EXAMPLE VIII

[N,N-Dibenzylaminoxymethyl]diisopropylamine

The procedure of Example I is repeated using 21.33 g of dibenzylhydroxylamine, 9.73 g of aqueous formaldehyde (37%) solution and 10.12 g of diisopropylamine, to afford the title compound.

Anal. Calcd. for $C_{21}H_{30}N_2O$: C, 77.3; H, 9.3; N, 8.6
Found: C, 77.6; H, 9.3; H, 8.4

EXAMPLE IX

[N,N-Dibenzylaminoxymethyl]diallylamine

The procedure of Example I is repeated using 21.33 g of dibenzylhydroxylamine, 9.73 g of aqueous formaldehyde (37%) solution and 9.72 g of diallylamine, to afford the title compound.

Anal. Calcd. for $C_{21}H_{26}N_2O$: C, 78.2; H, 8.1; N, 8.7 Found: C, 78.1; H, 8.2; H, 8.6

EXAMPLE X

[N,N-Dibenzylaminoxymethyl]-N-methyl-N-2-(pyridin-2-yl)ethylamine

The procedure of Example I is repeated using 21.33 g of dibenzylhydroxylamine, 9.73 g of aqueous formaldehyde (37%) solution and 13.62 g of 2-[2-(N-methylamino)ethyl]pyridine, to afford the title compound.

Anal. Calcd. for $C_{23}H_{27}N_3O$: C, 76.4; H, 7.5; N, 11.6 Found: C, 76.0; H, 7.4; H, 11.5

EXAMPLE XI

[N,N-Dibenzylaminoxymethyl]diphenylamine

The procedure of Example I s repeated using 21.33 g of dibenzylhydroxylamine, 9.46 g of aqueous formaldehyde (37%) solution and 16.92 g of diphenylamine, to afford the title compound as a colorless liquid with a mass spectrum, NMR and IR consistent with the desired structure.

EXAMPLE XII

[N,N-Dibenzylaminoxymethyl]-N-benzyl-N-exo-norbornylamine

The procedure of Example I s repeated using 21.33 g of dibenzylhydroxylamine, 9.73 g of aqueous formaldehyde (37%) solution and 20.13 g of 2-(benzylamino)norbornane, to afford the title compound.

Anal. Calcd. for $C_{27}H_{34}N_2O$: C, 81.7; H, 8.0; N, 6.6 Found: C, 81.6; H, 7.7; H, 6.5

EXAMPLE XIII

N',N'',N'''-Tris-[N,N-Dibenzylaminoymethyl]hexahydro-s-triazine

The procedure of Example I is repeated using 21.33 g of dibenzylhydroxylamine, 16.0 g of aqueous formaldehyde (37%) solution and 2.90 g of hexahydro-s-triazine, to afford the title compound.

EXAMPLE XIV

[N,N-Diethylaminoxymethyl]-di-n-butylamine

The procedure of Example I is repeated using 26.74 g of diethylhydroxylamine, 29.22 g of aqueous formaldehyde (37%) solution and 38.77 g of di-n-butylamine, to afford the title compound as a colorless liquid.

Anal. Calcd. for $C_{13}H_{30}N_2O$: C, 67.8; H, 13.1; N, 12.2 Found: C, 67.6; H, 13.5; H, 11.8

EXAMPLE XV

[N,N-Diethylaminoxymethyl]-diallylamine

The procedure of Example I is repeated using 26.74 g of diethylhydroxylamine, 10.81 g of aqueous formaldehyde (37%) solution and 29.15 g of diallylamine, to afford the title compound.

Anal. Calcd. for $C_{11}H_{22}N_2O$: C, 66.6; H, 11.2; N, 14.1. Found: C, 66.7; H, 10.8; N, 14.0.

EXAMPLE XVI

Processing of Polypropylene

| Base Formulation | |
|---|---|
| Polypropylene* | 100 parts |
| Calcium Stearate | 0.10 part |

*Profax 6501 from Himont U.S.A.

Stabilizers are solvent blended into polypropylene as solutions in methylene chloride and after removal of solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Gate #1 | 260 |
| Gate #2 | 260 |
| Gate #3 | 260 |
| RPM 100 | |

During extrusion, the internal extruder pressure is determined using a pressure transducer. After each of the first, third and fifth extrusions, resin pellets are compression molded into 125 mil (3.2 mm) thick plaques at 193° C. and specimen yellowness index (Y.I) determined according to ASTM D1925-63T.

The melt flow rate (MFR) is determined by ASTM method 1238 condition L. The melt flow rate varies inversely as the transducer pressure and both are a measure of the molecular weight for a specific type of polymer. The results are shown in the following tables.

| Series 1 Additives | Extrusion Temperature 260° C. YI Color After Extrusion | | | Melt Flow Rate After Extrusion (g/10 min.) | |
|---|---|---|---|---|---|
| | 1 | 3 | 5 | 1 | 5 |
| Base Resin | 2.5 | 3.5 | 4.7 | 6.3 | 14.9 |
| 0.1% Antioxidant A | 7.4 | 13.2 | 15.9 | 3.4 | 6.9 |
| 0.1% Antioxidant A + 0.5% Ex. II | 6.2 | 7.6 | 8.5 | 3.0 | 3.5 |
| 0.1% Antioxidant A + 0.05% Ex. IV | 4.7 | 6.0 | 6.7 | 3.4 | 4.2 |
| 0.1% Antioxidant A + 0.05% Ex. VII | 3.2 | 3.7 | 3.9 | 3.2 | 4.3 |
| 0.1% Antioxidant A + 0.05% Ex. VIII | 1.3 | 1.9 | 2.4 | 3.2 | 3.9 |

| Series 2 Additives | Extrusion Temp. 260° C. YI Color After Extrusion | | | Melt Flow Rate (g/10 min) After Extrusion | |
|---|---|---|---|---|---|
| | 1 | 3 | 5 | 1 | 5 |
| Base Resin | 1.8 | 2.5 | 3.5 | 5.0 | 9.9 |
| 0.1% Antioxidant A | 4.6 | 8.9 | 10.9 | 2.8 | 4.8 |
| 0.1% Antioxidant A + 0.05% Ex. XI | 2.6 | 3.6 | 6.2 | 2.4 | 3.4 |

| Series 3 Additives | Extrusion Temp. 260° C. YI Color After Extrusion | | | Melt Flow Rate (g/10 min) After Extrusion | |
|---|---|---|---|---|---|
| | 1 | 3 | 5 | 1 | 5 |
| Base Resin | 1.6 | 1.1 | 1.3 | 1.3 | 12.5 |
| 0.1% Antioxidant A | 6.0 | 11.7 | 14.6 | 4.0 | 5.9 |
| 0.1% Antioxidant A + 0.05% Ex. VI | 2.4 | 3.4 | 6.5 | 2.4 | 4.4 |
| 0.1% Antioxidant A + 0.05% Ex. XIV | 5.3 | 8.2 | 10.8 | 3.0 | 3.4 |

These data in the table thus indicate the effective color improving activity of the instant compounds.

Antioxidant A—Neopentyl tetrakis [3-(3',5'-di-tert-butyl-4'-hydroxyphenyl)propanoate]

EXAMPLE XVII

Light Stabilization of Polypropylene

Unstabilized polypropylene powder (Hercules Profax 6501) is thoroughly blended with the indicated amount of additive. The blended materials are then milled on a two-roll mill at 182° C. for 5 minutes, after which time the stabilized polypropylene is sheeted from the mill and allowed to cool. The milled polypropylene is then cut into pieces and compression molded on a hydraulic press at 250° C. and 175 psi ($1.2 \times 10^6$ Pa) into 25 mil plaques. The sample is exposed in a fluorescent sunlight/black light chamber until failure. Failure is taken as the hours required to reach 0.5 carbonyl absorbance by infrared spectroscopy on the exposed films.

| Additive | Additive Conc. (% by weight) | Hours to Failure |
|---|---|---|
| None | — | 100 |
| Example I | 0.2 | 320 |
| Example II | 0.2 | 320 |
| Example III | 0.2 | 290 |
| Example IV | 0.2 | 310 |
| Example V | 0.2 | 310 |
| Example VI | 0.2 | 200 |
| Example VIII | 0.2 | 280 |
| Example IX | 0.2 | 290 |
| Example X | 0.2 | 290 |
| Example XII | 0.2 | 270 |
| Example XIV | 0.2 | 230 |

These data thus indicate tha effective stabilization activity of the instant compounds.

EXAMPLE XVIII

Inhibition of Oxidation of Petroleum Turbine Oil

This test is performed according to ASTM procedure D943-81. 300 ml of 150 N paraffinic mineral oil containing 0.25% by weight of the test compound and 60 ml of distilled water are charged into a large glass tube and heated in an oil bath maintained at 95° C. Oxygen is bubbled at a rate of 3 liters per hour through the delivery tube and through the oil-water mixture. Iron-copper catalyst coils are mounted in the oxygen delivery tube. Samples of oil are removed periodically and the acid number determined. The oil under test is considered to have failed when an acid number of 2.0 has been attained. The test data are given below.

| Additive | Time (Hrs) | Acid Number |
|---|---|---|
| Base Oil (No stabilizer) | 90–100 | 2.0 |
| Compound of Example IV | 295 | 2.0 |

The instant compound is seen to stabilize the oil for a period in excess of the oxidation lifetime of the base oil.

EXAMPLE XIX

Engine Oil Thin Film Oxygen Uptake Test

This test is conducted in the standard rotary bomb apparatus (described in ASTM D-2272) with modifications in procedure as described in the Preprint No. 82 CC-10-1 presented at the Conference of the American Society of Lubrication Engineers, Oct. 5–7, 1982.

A 1.5 gram test sample of 150 N paraffinic mineral oil containing enough zinc dialkyldithiophosphate (ZDTP) to give 0.1% by weight of zinc and 0.5% by weight of the test compound is placed in the test apparatus. A catalyst package comprising 0.075 grams of oxidized fuel components, 0.075 grams of soluble metal catalyst* and 0.030 grams of water added. The temperature is set at 160° C. and the initial oxygen pressure is 90 psi. Failure is taken as the time in minutes for a pressure drop of 25 psi to be observed. The test results are given below.

| Additive | Failure Time (min.) |
|---|---|
| Base Oil (no stabilizer) | 105 |
| Compound of Example IV | 125 |

* The soluble metal catalysts are a mixture of the following metal naphthenates in the weight ratios given below: cupric 0.69%, ferric 0.41%, lead 8.0%, manganese 0.35%, stannous 0.36% (as naphthenates).

Summarizing, it is seen that this invention provides organic materials stabilized against degradation by the presence therein of various aminoxy alkylamines as well as various novel aminoxy alkylamine derivatives. Variations may be made in proportions, procedures and materials without departing from the scope of the invention as defined by the following claims.

What is claimed is:

1. A composition of matter comprising a plastic, polymer or resin subject to oxidative, thermal and actinic degradation stabilized with an effective stabilizing amount of a compound of the formula

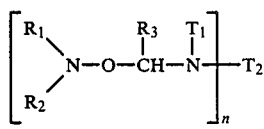

wherein
$R_1$ and $R_2$ are independently alkyl of 1 to 36 carbon atoms, cycloalkyl of 5 to 12 carbon atoms, aralkyl of 7 to 9 carbon atoms or said aralkyl substituted by alkyl of 1 to 36 carbon atoms, or $R_1$ and $R_2$ together with the nitrogen can form a piperidyl, pyrryl, morpholino or pyrrolidino ring, or $R_1$ and $R_2$ are independently a group of the formula

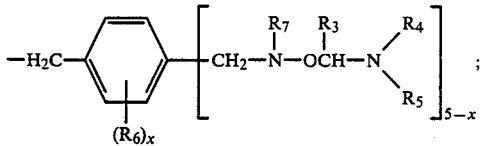

$R_3$, $R_4$, $R_5$, $R_6$ and $R_7$ are independently hydrogen, alkyl of 1 to 36 carbon atoms, cycloalkyl of 5 to 12 carbon atoms, allyl, aryl, aralkyl of 7 to 9 carbon atoms, said aralkyl substituted by alkyl of 1 to 36 carbon atoms, bornyl, norbornyl or isobornyl, or $R_4$ and $R_5$ together with the nitrogen can form a piperidyl, pyrryl, morpholino or pyrrolidino ring;

n is 1–4;

x is 0–5;

$T_1$ is $R_3$ or

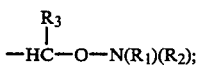

when n=1, $T_2$ is $R_3$ or pyridinyl-substituted ($C_1$–$C_4$) alkyl, or $T_1$ and $T_2$ together with the nitrogen can form a pyrrolidino, piperidyl or morpholino ring;

when n=2, $T_2$ is alkylene of 2 to 12 carbon atoms, cycloalkylene of 6 to 10 carbon atoms, arylene of 6 to 10 carbon atoms or alkylenearylenealkylene of 8 to 10 carbon atoms or $T_1$ and $T_2$ together with the two nitrogens can form a piperazine or pyrazolidine ring;

when n=3, $T_2$ is alkanetriyl of 3 to 6 carbon atoms or $T_1$ and $T_2$ together with the three nitrogens can form a fully saturated triazine or triazole ring; and when n=4, $T_2$ is alkanetetrayl of 4 to 6 carbon atoms.

2. The composition of claim 1, wherein $R_1$–$R_7$ are independently straight-chain or branched alkyl of 1 to 18 carbon atoms, cyclopentyl, cyclohexyl, benzyl, α-methylbenzyl or α,α-dimethylbenzyl.

3. The composition of claim 1, wherein $R_1$ and $R_2$ are benzyl and $R_3$ is hydrogen.

4. The composition of claim 1, wherein n=1, $T_1$ and $T_2$ are independently straight-chain or branched alkyl of 1 to 18 carbon atoms, cyclopentyl, cyclohexyl, allyl, phenyl, benzyl, α-methylbenzyl, or α,α-dimethylbenzyl or $T_1$ and $T_2$ together with the nitrogen form a morpholino, pyrrolidino or piperidyl ring.

5. The composition of claim 1, wherein n=2, $T_2$ is alkylene of 2 to 6 carbon atoms, phenylene or xylylene or $T_1$ and $T_2$ together with the nitrrgens form a piperazine ring.

6. The composition of claim 1, wherein n=3, $T_2$ is trimethylylpropane or $T_1$ and $T_2$ together with the nitrogens form a saturated triazine ring.

7. The composition of claim 1, wherein n=4 and $T_2$ is pentaerythrityl.

8. The composition of claim 5, wherein said compound is 1,4-bis[N,N-dibenzylaminoxymethyl]piperazine.

9. The composition of claim 5, wherein said compound is [N,N'-dimethyl-N,N'-bis(dibenzylaminoxymethyl)]hexamethylenediamine.

10. The composition of claim 4, wherein said compound is [N,N-dibenzylaminoxyethyl]di-n-butylamine.

11. The composition of claim 4, wherein said compound is [N,N-dibenzylaminoxymethyl]di-n-hexylamine.

12. The composition of claim 4, wherein said compound is [N,N-dibenzylaminoxymethyl]diisopropylamine.

13. The composition of claim 4, wherein said compound is [N,N-diethylaminoxymethyl]di-n-butylamine.

14. The composition of claim 1, wherein the polymer is a synthetic polymer.

15. The composition of claim 14, wherein the synthetic polymer is a polyolefin homopolymer or copolymer.

16. The composition of claim 15, which also contains a metal salt of a higher fatty acid.

17. The composition of claim 1 which also contains a phenolic antioxidant.

18. The composition of claim 16 which also contains a phenolic antioxidant.

19. The composition of claim 17, wherein said phenolic antioxidant is selected from the group consisting of n-octadecyl 3,5-di-tert-butyl-4-hydroxyhydrocinnamate, neopentanetetrayl tetrakis-(3,5-di-tert-butyl-4-hydroxylhydrocinnamate), di-n-octadecyl 3,5-di-tert-butyl-4-hydroxybenzyl-phosphonate, 1,3,5-tris(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)benzene, 3,6-di-oxaocta-methylene bis(3-methyl-5-tert-butyl-4-hydroxyhydro-cinnamate), 2,6-di-tert-butyl-p-cresol, 2,2'-ethylidene-bis(4,6-di-tert-butyl-phenol), 1,3,5-tris-(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydro-cinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-tert-butyl-4-hydroxyhydroxo-cinnamoyloxy)ethyl]-oxamide.

20. The composition of claim 19, wherein said phonolic antioxidant is neopentaretetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-tert-butyl-4-hydroxybenzylbenzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

21. A method for stabilizing a plastic, polymer or resin against oxidative, thermal and actinic degradation which comprises incorporating into said a plastic, polymer or resin effective stabilizing amount of a compound of claim 1.

* * * * *